United States Patent
Zelenka et al.

(10) Patent No.: US 10,905,851 B2
(45) Date of Patent: Feb. 2, 2021

(54) CATHETER SHEATH AND METHODS THEREOF

(71) Applicant: ACIST Medical Systems, Inc., Eden Prairie, MN (US)

(72) Inventors: Robert Zelenka, Milpitas, CA (US); Ruth E. Beeby, Mountain View, CA (US); Kendall R. Waters, Livermore, CA (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 16 days.

(21) Appl. No.: 13/833,919

(22) Filed: Mar. 15, 2013

(65) Prior Publication Data

US 2013/0253328 A1 Sep. 26, 2013

Related U.S. Application Data

(60) Provisional application No. 61/614,728, filed on Mar. 23, 2012.

(51) Int. Cl.
*A61M 25/00* (2006.01)
*A61B 8/12* (2006.01)
(Continued)

(52) U.S. Cl.
CPC .......... *A61M 25/0054* (2013.01); *A61B 8/12* (2013.01); *A61M 25/0009* (2013.01);
(Continued)

(58) Field of Classification Search
CPC .......... A61M 25/0013; A61M 25/0043; A61M 25/0053; A61M 25/0054; A61M 25/0141;
(Continued)

(56) References Cited

U.S. PATENT DOCUMENTS 4,582,181 A * 4/1986 Samson .......... A61M 25/09033
604/913
4,636,346 A 1/1987 Gold et al.
(Continued)

FOREIGN PATENT DOCUMENTS

CN 1810213 A 8/2006
EP 1955724 A1 8/2008
(Continued)

OTHER PUBLICATIONS

International Search Report and Written Opinion of PCT/US2012/037626, dated Feb. 26, 2013, 10 pages, Korean Intellectual Property Office, Daejeon Metropolitan City, Republic of Korea.
(Continued)

*Primary Examiner* — Manuel A Mendez
*Assistant Examiner* — Justin L Zamory
(74) *Attorney, Agent, or Firm* — Fredrikson & Byron, P.A.

(57) ABSTRACT

A catheter a first sheath having a proximal end and a distal end, and a length extending between the proximal end and the distal end. The first sheath being devoid of any bonds between the proximal end and the distal end, and a flexural modulus of the first sheath varying along the length. A method of making a catheter having more than one flexural modulus.

28 Claims, 5 Drawing Sheets

(51) Int. Cl.
*B29C 71/00* (2006.01)
*B29C 71/02* (2006.01)

(52) U.S. Cl.
CPC ..... *A61M 25/0012* (2013.01); *B29C 71/0063* (2013.01); *B29C 2071/022* (2013.01)

(58) Field of Classification Search
CPC .......... A61M 25/0009; A61M 25/0012; B29C 71/0063
See application file for complete search history.

(56) References Cited

U.S. PATENT DOCUMENTS

| | | | |
|---|---|---|---|
| 4,870,887 A | 10/1989 | Tressler et al. | |
| 4,976,690 A * | 12/1990 | Solar | A61M 25/0054 604/103.06 |
| 5,037,404 A | 8/1991 | Gold et al. | |
| 5,201,316 A | 4/1993 | Pomeranz et al. | |
| 5,240,985 A | 8/1993 | Gardiner et al. | |
| 5,250,069 A | 10/1993 | Nobuyoshi et al. | |
| 5,312,356 A | 5/1994 | Engelson et al. | |
| 5,316,706 A * | 5/1994 | Muni | A61M 25/0009 264/209.1 |
| 5,330,444 A | 7/1994 | Webler et al. | |
| 5,399,164 A | 3/1995 | Snoke et al. | |
| 5,400,785 A | 3/1995 | Crowley | |
| 5,443,457 A | 8/1995 | Ginn et al. | |
| 5,531,721 A | 7/1996 | Pepin et al. | |
| 5,538,512 A | 7/1996 | Zenzen et al. | |
| 5,542,924 A | 8/1996 | Snoke et al. | |
| 5,584,821 A | 12/1996 | Hobbs et al. | |
| 5,624,397 A | 4/1997 | Snoke et al. | |
| 5,715,825 A | 2/1998 | Crowley | |
| 5,720,300 A | 2/1998 | Fagan et al. | |
| 5,762,066 A | 6/1998 | Law et al. | |
| 5,824,030 A | 10/1998 | Yang et al. | |
| 5,851,203 A * | 12/1998 | van Muiden | A61M 25/0054 138/125 |
| 5,957,910 A | 9/1999 | Holden et al. | |
| 6,007,478 A * | 12/1999 | Siess et al. | 600/16 |
| 6,126,650 A | 10/2000 | Martinez et al. | |
| 6,180,059 B1 | 1/2001 | Divino, Jr. et al. | |
| 6,264,633 B1 | 7/2001 | Knorig | |
| 6,454,997 B1 | 9/2002 | Divino, Jr. et al. | |
| 6,524,303 B1 | 2/2003 | Garibaldi | |
| 6,610,068 B1 | 8/2003 | Yang | |
| 6,648,024 B2 | 11/2003 | Wang | |
| 6,676,900 B1 | 1/2004 | Divino, Jr. et al. | |
| 6,712,766 B2 | 3/2004 | Harada | |
| 6,929,635 B2 | 8/2005 | Shelso | |
| 7,332,236 B2 | 2/2008 | Ballantine et al. | |
| 7,387,826 B2 | 6/2008 | Burgmeier et al. | |
| 7,632,236 B2 | 12/2009 | Kaneto et al. | |
| 2002/0188189 A1 | 12/2002 | Belef et al. | |
| 2003/0141002 A1 * | 7/2003 | Flanagan | B23K 26/03 156/64 |
| 2003/0195490 A1 | 10/2003 | Boatman et al. | |
| 2003/0236495 A1 * | 12/2003 | Kennedy, II | A61M 25/10 604/97.02 |
| 2004/0073158 A1 | 4/2004 | Shah | |
| 2005/0090852 A1 | 4/2005 | Layne et al. | |
| 2005/0101859 A1 | 5/2005 | Maschke | |
| 2005/0125002 A1 | 6/2005 | Baran et al. | |
| 2005/0142314 A1 | 6/2005 | Burgmeier et al. | |
| 2005/0154442 A1 | 7/2005 | Eidenschink et al. | |
| 2005/0203396 A1 | 9/2005 | Angelsen et al. | |
| 2005/0261586 A1 | 11/2005 | Makin et al. | |
| 2006/0084964 A1 | 4/2006 | Knudson et al. | |
| 2007/0134305 A1 | 6/2007 | Ziberman | |
| 2007/0167824 A1 | 7/2007 | Lee et al. | |
| 2007/0240817 A1 * | 10/2007 | Strong | A61M 25/0009 156/304.3 |
| 2007/0244501 A1 | 10/2007 | Horn et al. | |
| 2008/0109057 A1 * | 5/2008 | Calabria | A61B 17/12022 623/1.11 |
| 2009/0163818 A1 | 6/2009 | Zelenka et al. | |
| 2009/0270737 A1 * | 10/2009 | Thornton | A61B 8/12 600/466 |
| 2009/0297582 A1 | 12/2009 | Meyer | |
| 2010/0063477 A1 | 3/2010 | Ohigawa | |
| 2010/0152590 A1 | 6/2010 | Moore et al. | |
| 2010/0185172 A1 | 7/2010 | Fabro | |
| 2010/0204605 A1 | 8/2010 | Blakley et al. | |
| 2011/0009938 A1 * | 1/2011 | Dowling | A61N 1/056 607/119 |
| 2011/0091515 A1 | 4/2011 | Zilberman et al. | |
| 2012/0277772 A1 | 11/2012 | Aben et al. | |
| 2012/0289837 A1 | 11/2012 | Zelenka | |
| 2015/0272732 A1 | 10/2015 | Tilson et al. | |

FOREIGN PATENT DOCUMENTS

| | | |
|---|---|---|
| JP | H05-084247 A | 4/1993 |
| JP | H08-57035 A | 3/1996 |
| JP | H08-140976 A | 6/1996 |
| JP | H08-275947 A | 10/1996 |
| JP | 2000152940 A | 6/2000 |
| JP | 2002109217 A | 4/2002 |
| JP | 2002528188 A | 9/2002 |
| JP | 2003210462 A | 7/2003 |
| JP | 3571939 B2 | 9/2004 |
| JP | 2005013453 A | 1/2005 |
| JP | 2005052667 A | 3/2005 |
| JP | 2006075611 A | 3/2006 |
| JP | 2007152101 A | 6/2007 |
| JP | 2012024491 A | 2/2012 |
| WO | 9221965 A1 | 12/1992 |
| WO | 9414494 A2 | 7/1994 |
| WO | 9714466 A1 | 4/1997 |
| WO | 1998050098 A1 | 11/1998 |
| WO | 0033742 A2 | 6/2000 |
| WO | 2009134171 A1 | 11/2009 |
| WO | 2011027821 A1 | 3/2011 |
| WO | 2013169269 A1 | 11/2013 |

OTHER PUBLICATIONS

International Preliminary Report on Patentability from International Patent Application No. PCT/US2013/033227, dated Sep. 13, 2014, 6 pages.
U.S. Appl. No. 61/484,941, entitled "Variable-Stiffnes Imaging Window and Production Method Thereof," filed May 11, 2011, 19 pages.
T.W. Giants, "Crystallinity and Dielectric Properties of PEEK, Poly (ether ether ketone)," IEEE Transactions on Dielectrics and Electrical Insulation, vol. 1 No. 6 (1994), Abstract.
S.M. Kurtz and J.N. Devine, "PEEK Biomaterials in Trauma, Orthopedic, and Spinal Implants," Biomaterials, 28(32):4845-4869 (2007).
PCT/US2013/033227, International Search Report and Written Opinion dated Jun. 12, 2013, 8 pages.

* cited by examiner

CATHETER SHEATH AND METHODS THEREOF

RELATED APPLICATIONS

The present application claims the benefit of U.S. Provisional Application Ser. No. 61/614,728, titled Catheter Sheath and Methods Thereof, filed Mar. 23, 2012, the contents of which are incorporated by reference.

FIELD

The present disclosure relates to catheters, such as intravascular catheters, having sheaths with variable stiffness.

BACKGROUND

Catheters are used to access patients and diagnose and treat diseases. For example, patients suffering from coronary artery disease may receive percutaneous coronary interventions for treatment of the disease. An intravascular imaging catheter may be used to evaluate the coronary artery disease as well as guide the selection of treatment devices.

Catheters, such as intravascular imaging catheters, have multiple sections that have different flexural moduli, or stiffnesses, to balance catheter pushability and catheter trackability. Pushability describes how a force transmitted longitudinally at the catheter proximal end is transferred to longitudinal movement of the catheter distal end. Trackability describes how easily the catheter is able to reach its destination (e.g., a coronary artery segment). Multiple catheter sheath sections are generally joined using a bonding technique, such as thermal or adhesive bonding. Each catheter sheath joining section may act as a hinge point as the catheter is delivered through tortuous anatomy. Current intravascular imaging catheters exhibit limitations, such as prolapsing, in navigating tortuous coronary arteries.

SUMMARY

In embodiments described herein, a catheter includes a sheath having variable flexural moduli along its length. In some embodiments, the sheath includes at least two sections wherein the flexural moduli of the sheath sections are different. The sheath may comprise a polymer. In such embodiments, the polymer sheath may be processed in order to have at least two sections of different flexural moduli. Some embodiments include a method to process a polymer sheath to have at least two sections of different flexural moduli. Embodiments of the invention also include a catheter having a sheath with at least two sections of different flexural moduli and no bond joints can provide improved pushability and trackability, which may be particularly useful for intravascular catheters.

BRIEF DESCRIPTION OF THE DRAWINGS

The following drawings are illustrative of particular embodiments of the invention and therefore do not limit the scope of the invention. The drawings are not necessarily to scale (unless so stated) and are intended for use in conjunction with the explanations in the following detailed description. Embodiments of the invention will hereinafter be described in conjunction with the appended drawings, wherein like numerals denote like elements.

DETAILED DESCRIPTION OF THE EMBODIMENTS

Figure 1:
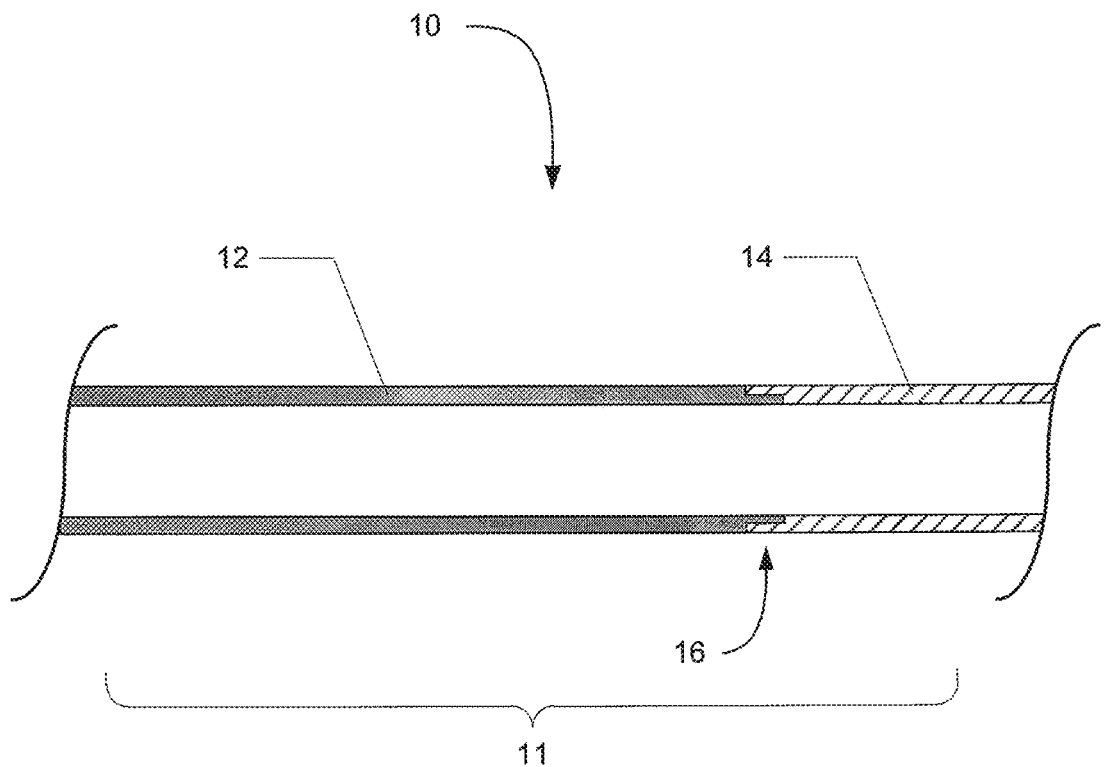
FIG. 1 is a sectional side view of a prior art catheter having multiple sheath sections.

FIG. 1 shows a sectional side view of a prior art catheter 10 having a sheath with stiffness that varies with length. The catheter 10 includes a proximal sheath 12, a distal sheath 14, and a bond region 16. The proximal sheath 12 may be bonded to the distal sheath 14 by thermal bonding. The proximal sheath 12 may have a flexural modulus in the range 500 ksi (kilopound per square inch) to 1600 ksi, generally 595 ksi. The distal sheath 14 may have a flexural modulus in the range 200 ksi to 250 ksi, generally 225 ksi. The flexural modulus of the distal sheath 14 is generally smaller than the flexural modulus of the proximal sheath 12. Accordingly, the catheter sheath assembly has increasing flexibility on bonded sheaths progressing distally (i.e., from left to right in FIG. 1). The progressive flexibility of the catheter sheath 10 may be advantageous for catheter pushability and trackability. However, the transition in flexural modulus across the proximal-to-distal bond region 16, from 595 ksi to 225 ksi, may be problematic for some applications, such as intracoronary applications. The bond region 16 may act as an undesirable hinge point when delivering the catheter to a coronary artery having tortuous anatomy causing the catheter to prolapse. Further, for intracoronary imaging catheters, such as an intravascular ultrasound imaging catheter having a mechanically rotating imaging core, prolapsing at the hinge point can degrade image quality if the prolapse constrains the motion of the mechanically rotating imaging core.

Figure 2:
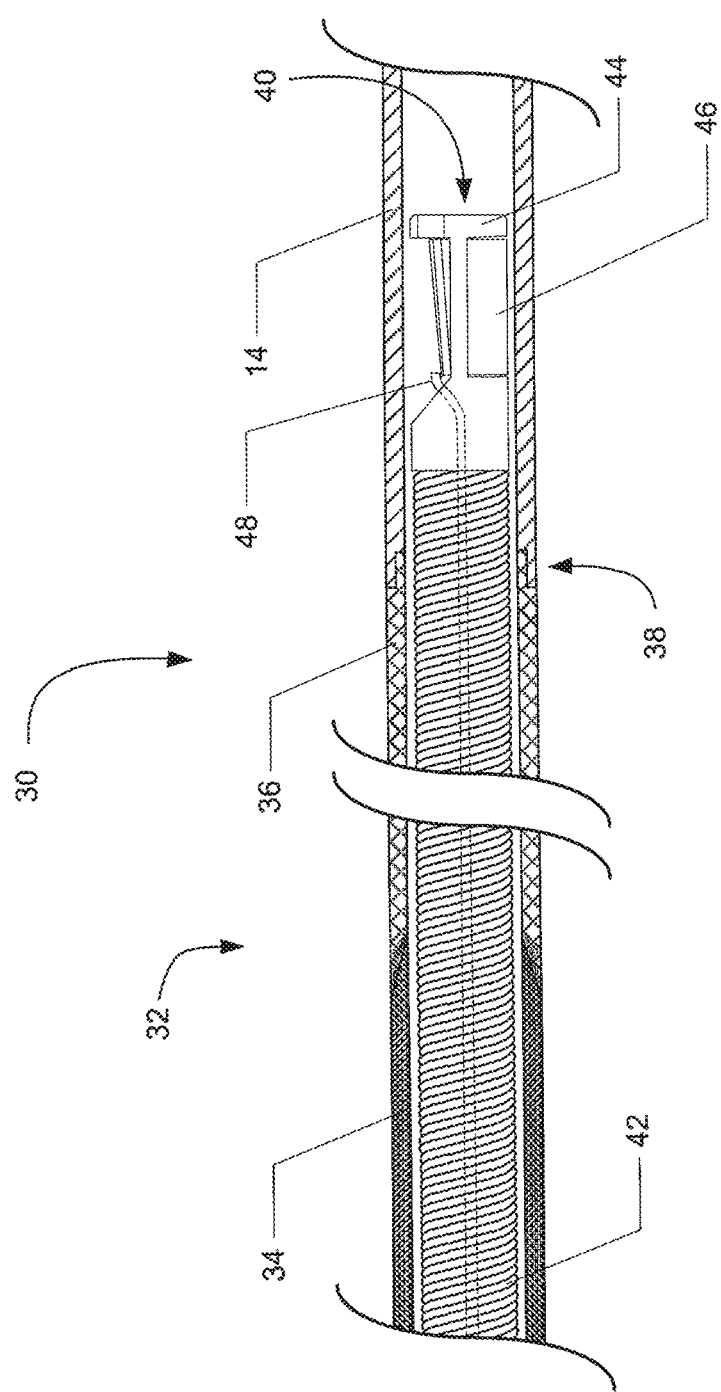
FIG. 2 is partial sectional side view of a catheter in accordance with an embodiment of the invention.

Referring now to FIG. 2, a partial sectional side view of a catheter 30 according to one embodiment of the invention is shown. For illustrative purposes only, embodiments of the invention described herein are appropriate for intracoronary ultrasound imaging catheters. The described embodiments do not limit application of the invention to only intracoronary catheters or ultrasound imaging catheters. In the embodiment shown, catheter 30 includes a proximal sheath 32, a distal sheath 14, a bond region 38, and an imaging core 40. Also in the embodiment shown, the imaging core 40 further includes a flexible drive cable 42, a transducer housing 44, an ultrasonic transducer stack 46, and a transmission line 48.

The distal sheath can comprise any suitable material. In some embodiments, the distal sheath 14 can include a polymer, such as a biocompatible polymer. In certain embodiments, the distal sheath 14 may comprise a polyethylene, such as a high-density polyethylene (HDPE), a low-density polyethylene (LDPE), or a blend of HDPE and LDPE.

The distal sheath 14 may also be provided with any desired flexural modulus. For example, the distal sheath may have a flexural modulus between about 5 and about 500 ksi, such as between about 35 ksi and about 250 ksi. In some embodiments, the distal sheath 14 has a flexural modulus of between about 150 ksi and about 300 ksi near the bond region, such as between about 200 ksi and 250 ksi (e.g. about 225 ksi) near the bond region 38.

In some embodiments, the distal sheath 14 may be of a form as described for example in additional detail in U.S. Patent Application Ser. No. 61/484,941 and US Publication No. 2012/0289837 by Zelenka and Costa, the complete disclosure of each of which is hereby incorporated herein by reference. For example, the distal sheath 14 can include an ultrasound imaging window. The ultrasonic attenuation of the ultrasound imaging window is sufficiently low such that the ultrasound imaging window is substantially transparent to ultrasound energy.

The proximal sheath can have a proximal end, a distal end, and a length extending between the proximal and distal ends. The proximal sheath can comprise any suitable material capable of having different flexural moduli along the sheath's length. In some embodiments, the proximal sheath can include a polymer, such as a biocompatible polymer. In certain embodiments of the invention, the polymer can be semi-crystalline or semi-amorphous. In some embodiments, the proximal sheath can comprise, consist essentially of, or consist of a polymer having a crystallinity that can be modified by heat treatment. In certain embodiments, the proximal sheath 32 comprises, consists essentially of, or consists of polyetheretherketone (PEEK™). In some embodiments, the PEEK is processed to have different crystallinities and flexural moduli. For example, a local region of an amorphous PEEK extrusion can be heat-treated to increase the crystallinity and flexural modulus of the local region.

PEEK polymers have a glass transition temperature generally in the range of 143° C. to 158° C., and a melting point generally in the range of 334° C. to 344° C. The crystallinity of PEEK can be modified by thermal annealing a PEEK material above its glass transition temperature and below its melting point, wherein higher annealing temperatures may result in a higher crystallinity and, consequently, a higher flexural modulus.

As shown in FIG. 2, the proximal sheath 32 can include at least a first section 34 and a second section 36, wherein the first section 34 is proximal to the second section 36. In some embodiments, the first section 34 has a different flexural modulus than the second section 36. In certain embodiments, the first section 34 has a higher flexural modulus than the second section 36. For example, the first section 34 of the proximal sheath 32 may have a flexural modulus in the range of about 500 ksi to about 1600 ksi, such as about 550 ksi to about 650 ksi (e.g., about 595 ksi). The second section 36 of the proximal sheath 32 may for example have a flexural modulus in the range of about 200 ksi to about 400 ksi, such as about 250 ksi to about 350 ksi (e.g., about 300 ksi).

In some embodiments, the first section 34 has a different crystallinity than the second section 36. In certain embodiments, the first section 34 has a higher crystallinity than the second section 36. For example, the first section 34 of the proximal sheath 32 may have a crystallinity in the range of between about 10% and about 40% (e.g., between about 20% and about 30%). The second section 36 of the proximal sheath 32 may for example have a crystallinity in the range between about 0% and about 20% (e.g., between about 0% and about 10%). In some embodiments, such as embodiments including PEEK, the higher crystallinity of the first section 34 provides a higher flexural modulus than the flexural modulus of the second section 36, such that the crystallinity and flexural modulus of the proximal sheath 32 decrease in the proximal to distal direction.

Figure 2A:
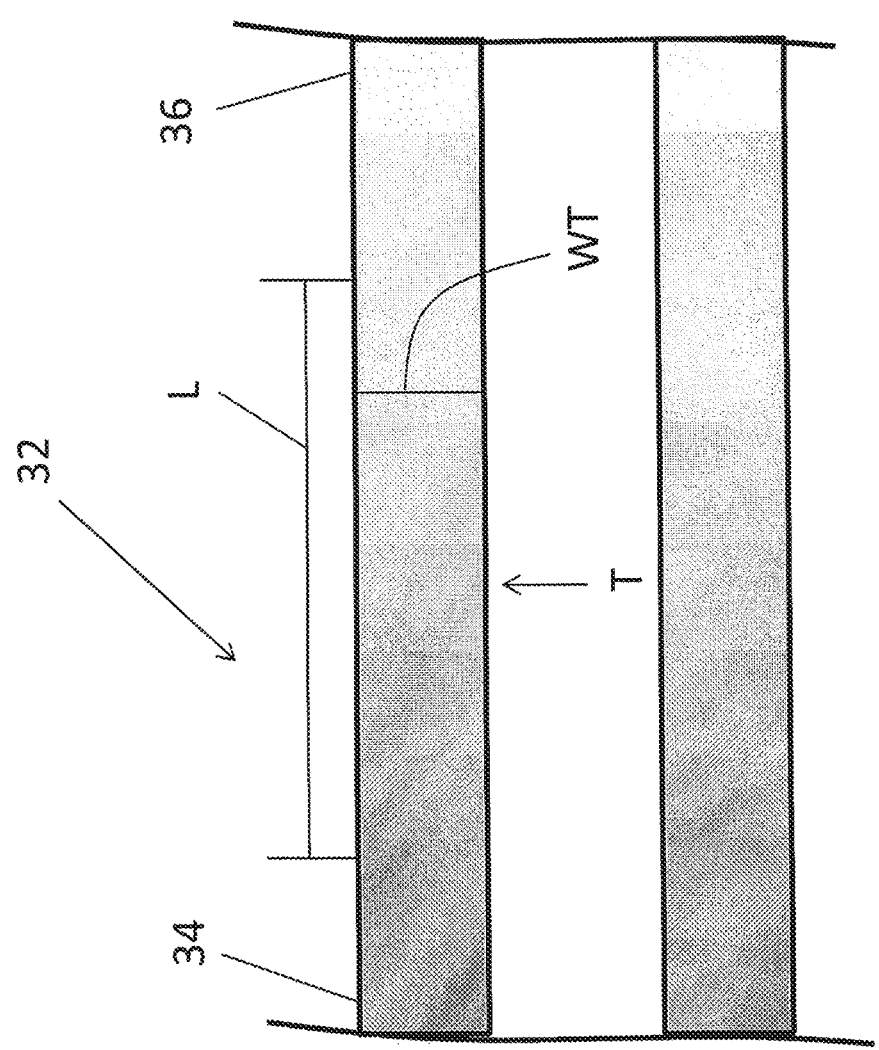
FIG. 2A is partial sectional side view of a proximal sheath in accordance with an embodiment of the invention.

In general, there is no bond region between the first section 34 and the second section 36 and, in some embodiments, no discrete location where the first section terminates and the second section begins. Rather, the transition between the first section and the second section can be continuous gradient across a longitudinal distance of the catheter, an embodiment of which is shown in FIG. 2. Such a gradient can be referred to as a transition region. FIG. 2A shows an embodiment of a transition region T for a proximal sheath 32 having a first section 34 and a second section 36. In FIG. 2A, transition region T is represented by darker shading to the left of the figure than the right of the figure. Such shading represents a change in a physical property, such as flexural modulus, in a same material rather than a change in composition of material. As shown, the transition region T can transition from a first physical property (e.g., a first flexural modulus and/or a first crystallinity) to a second physical property (e.g., a second flexural modulus and/or a second crystallinity) gradually over a length L of the sheath, where the first physical property is different than the second physical property. In some embodiments, there are no sharp lines of demarcation between first section 34 and second section 36. In certain embodiments, the length L of the transition region T is at least as great as a wall thickness WT of the sheath. In other embodiments, the length L is at least two times the wall thickness WT. In yet other embodiments, the length L is at least three times the wall thickness WT. In some embodiments, the length L is at least four (e.g., five) times the wall thickness WT.

Accordingly, in some embodiments, the first and second sections can have the same composition, but have different flexural moduli because they have been processed differently. In certain embodiments, the transition between the first section and the second section has a flexural modulus gradient between the flexural modulus of the first section and the flexural modulus of the second section. Such embodiments provide a proximal sheath having a varying flexural modulus without a bond joint that could potentially lead to catheter prolapse at the bond joint during catheter delivery under tortuous anatomy conditions. In certain embodiments physical properties other than flexural moduli may also change across the transition although the composition remains the same. Such other physical properties can include specific gravity and optical transparency. In certain embodiments comprising PEEK, specific gravity can change from about 1.3 grams (g)/cubic centimeter (cc) to about 1.26 g/cc across the transition from semi-crystalline to semi-amorphous, and can change from opaque to semi-transparent across the transition from semi-crystalline to semi-amorphous.

The proximal sheath may be provided in any suitable size. In some embodiments, the outer diameter of the proximal sheath 32 may be constant in the range of about 0.034" to about 0.060" (e.g., about 0.046"). In certain embodiments, the proximal sheath 32 is sufficiently small for the catheter to be delivered through a 6 F guide catheter. Further, the inner diameter of the proximal sheath 32 may be constant in the range of about 0.024" to about 0.040" (e.g., about 0.032"). The proximal sheath wall thickness may be in the range of about 0.001" to about 0.010" (e.g., about 0.007").

The proximal sheath may also be provided in any suitable length, depending, in part on the access point to the patient and the procedure to be performed. As an example, the length of a proximal sheath depends in part on the distance from an access point, such as a femoral artery, to a coronary ostium for access to a coronary artery. In some embodiments, the length of the proximal sheath 32 may be in the range of about 100 cm to about 150 cm (e.g., about 125 cm).

Further, the first and second sections 34, 36 can each have any desired length. For certain cardiovascular applications, the first section will generally be longer than the more distally located second section. For example, in some embodiments the first section has a length of at least three times the length of the second section. In other embodiments, the first section has a length of at least four times the length of the second section. In yet other embodiments, the first section has a length of at least five times the length of the second section. As a non-limiting example, for a proximal sheath with a length of 125 cm, the first section may be the proximal 109 cm, and the second section may be the distal 16 cm.

In some embodiments, the proximal sheath 32 can be coupled with the distal sheath 14 by any suitable method, such as by bonding. For example, a proximal sheath can be bonded to a distal sheath with a medical device adhesive. Accordingly, in some embodiments the catheter sheath will include a proximal sheath having more than one flexural moduli bonded to a distal sheath. In a particular embodiment, the catheter sheath will include a proximal sheath comprising PEEK and having more than one flexural moduli bonded to a distal sheath comprising polyethylene.

In some embodiments a proximal sheath having different sections with different flexural moduli allows for a relatively small difference in flexural moduli between the distal most section of the proximal sheath and the distal sheath. In certain embodiments, the difference in flexural moduli across the bond region 38 is less than about 150 ksi. In other embodiments, the difference in flexural moduli across the bond region 38 is less than about 100 ksi. In yet other embodiments, the difference in flexural moduli across the bond region 38 is about 75 ksi or less. In a specific example, the distal most section of the proximal sheath may have a flexural modulus of about 300 ksi and the proximal sheath may have a flexural modulus of about 225 ksi, providing a difference in flexural moduli across the proximal-to-distal bond region 38 between the second section 36 of the proximal sheath 32 and the distal sheath 14 of 75 ksi. This relatively small transition in flexural modulus across the proximal-to-distal bond region 38 can help reduce risk of potential catheter prolapse.

Embodiments of catheter sheaths in accordance with the invention can be made by any suitable method. In general, methods in accordance with embodiments of the invention include providing a catheter sheath having a length, and processing the catheter sheath differently along its length to produce a catheter sheath having different flexural moduli along its length. In one embodiment, such a proximal sheath can be processed by the application of different heat treatments along its length to produce different flexural moduli along its length. In such embodiments, applying localized heat treatments to a proximal sheath having a uniform flexural modulus along its length can produce a proximal sheath having two or more sections with different flexural moduli and no bond joints between the sections. Any number of different sections can be created by applying different heat treatment to different longitudinal locations, as desired.

In certain embodiments, the heat treatments change the crystallinity of the treated portions of the proximal sheath, thereby changing the flexural modulus. For example, localized heating of a proximal sheath comprising a previously amorphous polymer (e.g., PEEK) can cause crystallization of the previously amorphous polymer. Different degrees of crystallization, having different flexural moduli, can be imparted to different sections of the proximal sheath depending on the heat treatment applied.

Figure 3:
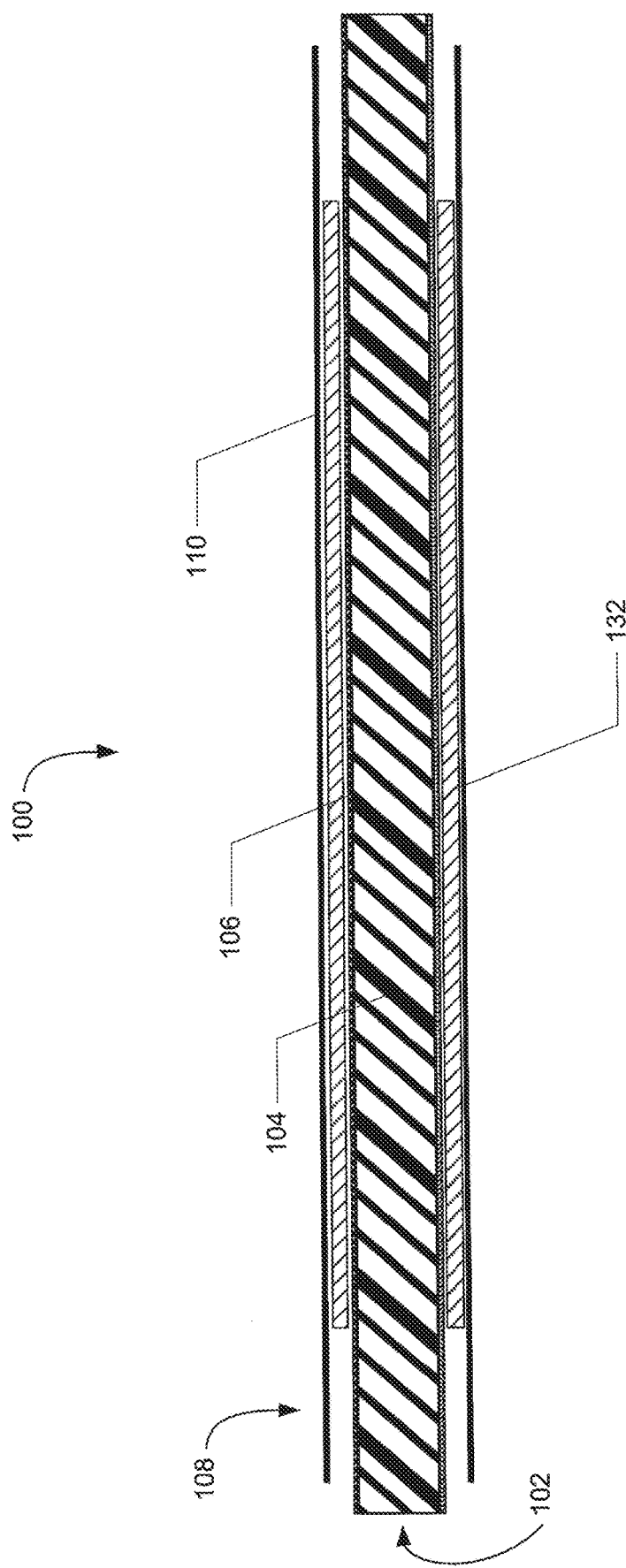
FIG. 3 is a sectional side view of a catheter sheath assembly fixture in accordance with an embodiment of the invention.
Figure 4:
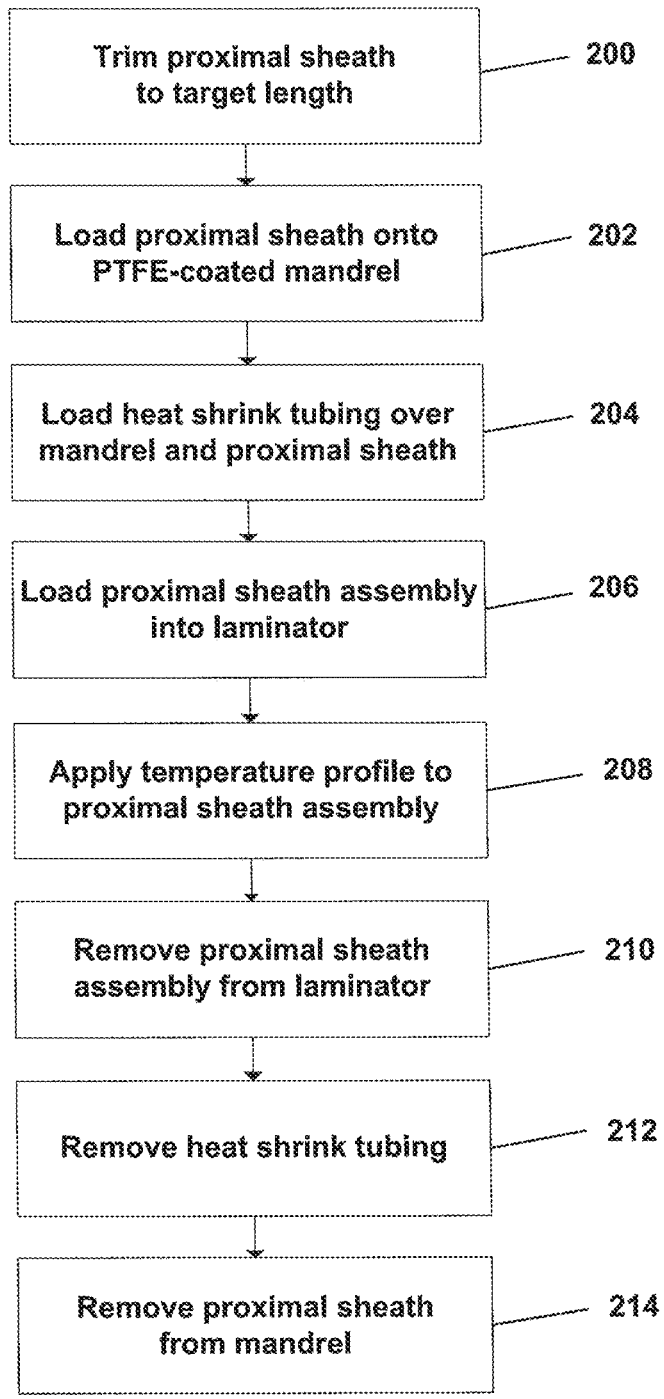
FIG. 4 is a flow diagram illustrating exemplary processing steps for manufacturing a catheter sheath in accordance with an embodiment of the invention.

The heat treatments can be applied in any suitable manner. A representative proximal sheath assembly fixture 100 is shown in sectional side view in FIG. 3. A flow diagram illustrating exemplary processing steps for manufacturing a proximal sheath embodying the invention is shown in FIG. 4. For convenience, the exemplary method will be described with respect to heat treatment with a laminator heater, such as a Beahm Designs catheter laminating machine. However, the method is not particularly limited to the application of heat with a laminator heater, or even to hot air technology generally. In other embodiments, other heating technologies may be used, such as a hot box, a laser, or an infrared heat source. The following method represents one embodiment of the production method.

As shown, a coated mandrel 102 can include a mandrel 104 and a thin anti-stick coating 106 (e.g., polytetrafluoroethylene (PTFE)). The coated mandrel may have any size useful for loading a proximal sheath, such as any of the embodiments of proximal sheaths described herein. In some embodiments, the mandrel has a diameter in the range of about 0.0225" to about 0.0385" (e.g., about 0.0315"). The coated mandrel 102 may be used for loading of a proximal sheath 132.

In some embodiments, the proximal sheath 132 can be trimmed in step 200. In certain embodiments, it is trimmed to a length in the range of about 100 cm to about 150 cm (e.g., about 125 cm). The trimmed proximal sheath 132 can be loaded onto the mandrel 102 in step 202. The proximal end (i.e., left side in FIG. 3) of the proximal sheath 132 may be positioned in the range of about 100 mm to about 150 mm (e.g., about 125 mm) from an end of the coated mandrel 102. The distance from the end of the coated mandrel 102 to the proximal end of the proximal sheath 132 can be referred to as a top clamping region 108. The length of the top clamping region 108 can be sufficiently long such that a laminator clamp does not clamp the proximal sheath 132.

In some embodiments, tubing 110 (e.g., heat shrink tubing) can be next loaded over the proximal sheath 132 and the top clamping region 108 of the coated mandrel 102 in step 204. Such tubing 110 may be useful for providing a buffer layer between the catheter sheath and a heat source. The tubing 110 may comprise fluorinated ethylene propylene (FEP). The tubing 110 may have an inner diameter in the range of about 0.042" to about 0.048" (e.g., about 0.045"). In certain embodiments, the length of the tubing 110 can be sufficient to cover the length of the top clamping region 108 and the proximal sheath 132, for example, at least about 125 cm.

Next, in some embodiments the proximal sheath assembly fixture 100, including the coated mandrel 102, the proximal sheath 132, and the heat shrink tubing 110, is loaded into a laminator in step 206 wherein the top clamping region 108 can be fixed in position by means of a laminator clamp.

In step 208 heat can be applied to a first section of the proximal sheath assembly 100. In one embodiment, a first section of the (amorphous PEEK) proximal sheath 132 (i.e., left end in FIG. 3) comprising amorphous PEEK is heated to about 154° C. In certain embodiments, the sheath is heated to this temperature throughout its thickness. The heating may cause the crystallinity to increase to about 35%, and the flexural modulus of the first section of the proximal sheath 132 may correspondingly increase to about 595 ksi. A second section of the (amorphous PEEK) proximal sheath may not receive heat treatment, and may remain amorphous. Different heat treatments may be applied to different lengths of the proximal sheath to create multiple sections (e.g., 2, 3, 4, 5, n) of the proximal sheaths, each having a different flexural modulus. For embodiments in which the heat is applied with a laminator, the amount of time the first section is exposed to the heat can depend on the temperature and speed of the laminator. In certain embodiments, the first section is exposed to the heat for about 1 second or less. In some embodiments, the laminator may have a temperature below that of the melting point of the material of the sheath. In some embodiments, the laminator has a temperature of between about 154° C. and about 204° C.

After the proximal sheath assembly 100 is heat-treated, it can be removed from the laminator in step 210. In steps 212 and 214, the tubing 110 can be removed from the proximal sheath assembly 100, and the heat-treated proximal sheath 132 can be removed from the mandrel, respectively.

Referring now to FIG. 2, such an exemplary process will produce a catheter 30 with a proximal sheath 32 having first and section sections 34, 36. In a specific embodiment comprising PEEK, the first section 34 of the proximal sheath 32 can have a crystallinity of about 35% and a flexural modulus of about 595 ksi. The second section 36 of the PEEK proximal sheath 32, which is distal to the first section 34, can remain amorphous with a crystallinity of less than about 10% and a flexural modulus of about 300 ksi. Such a catheter is useful for traversing tortuous pathways.

In some embodiments, an additional processing step can be employed when the proximal sheath is loaded on the coated mandrel to further increase the crystallinity of a polymer (e.g., PEEK) for a given heat treatment. For example, a tensile stress can be applied to the proximal sheath prior to or during a heat treatment step. In some embodiments, the proximal sheath can be held in a generally vertical orientation when it is exposed to heat. In such embodiments, a weight can be coupled to the bottom of the sheath to impart the tensile stress. In some embodiments, a tensile stress of about 50% to about 75% of the material's tensile strength at break can be applied. In certain embodiments comprising PEEK, which has a tensile strength at break of about 120 Megapascal (MPa), an applied tensile stress can be about 60 MPa to about 90 MPa.

While particular embodiments of the present invention have been shown and described, modifications may be made, and it is therefore intended to cover all such changes and modifications which fall within the true spirit and scope of the invention.

What is claimed is:

1. A catheter, comprising:
   a first sheath having a proximal end and a distal end, and a length extending between the proximal end and the distal end, the first sheath being devoid of any bonds between the proximal end and the distal end, the first sheath having a transition region including a change in a flexural modulus of the first sheath along a portion of the length, the transition region being between a first section with a first flexural modulus and a second section with a second flexural modulus, the first flexural modulus being greater than the second flexural modulus and the first section being proximal of the second section, and the transition region having a transition region length equal to at least four times a thickness of a wall of the first sheath,
   wherein the distal end of the first sheath is bonded to a second sheath at a bond region, wherein the second sheath has a flexural modulus and the difference in flexural moduli across the bond region is about 75 ksi or less, wherein the first sheath comprises a different polymer material than the second sheath, wherein the second sheath comprises an ultrasound imaging window that is substantially transparent to ultrasound energy, and wherein the second sheath has an outer diameter that is constant along a length of the ultrasound imaging window.

2. The catheter of claim 1, wherein the change in the flexural modulus of the first sheath at the transition region between the first section and the second section comprises a continuous gradient along the transition region length.

3. The catheter of claim 1, wherein the first section comprises the same material as the second section.

4. The catheter of claim 1, wherein the first section and the second section comprise a polymer.

5. The catheter of claim 4, wherein the first section and the second section comprise a polyetheretherketone.

6. The catheter of claim 5, wherein the crystallinity of the first section is between about 10% and about 40%.

7. The catheter of claim 1, wherein the first section is at least three times the length of the second section.

8. The catheter of claim 1, wherein the first sheath comprises polyetheretherketone.

9. The catheter of claim 1, wherein an outer diameter of the first sheath is constant along the length, and wherein the outer diameter of the second sheath equals the outer diameter of the first sheath.

10. The catheter of claim 1, wherein an inner diameter of the first sheath is constant along the length.

11. The catheter of claim 1, wherein a thickness of the first sheath is constant along the length.

12. The catheter of claim 8, wherein the second sheath comprises a polyethylene.

13. The catheter of claim 1, wherein the catheter is an ultrasound imaging catheter further including an imaging core in the second sheath.

14. The catheter of claim 13, wherein the imaging core further includes a flexible drive cable, a transducer housing, an ultrasonic transducer stack, and a transmission line.

15. The catheter of claim 1, wherein the first sheath is bonded to the second sheath by an adhesive.

16. The catheter of claim 1, wherein the first section is longer than the second section such that the transition region is closer to the distal end of the first sheath than to the proximal end of the first sheath.

17. A catheter, comprising:
   a first sheath having a proximal end and a distal end; and a length extending between the proximal end and the distal end, the first sheath being devoid of any bonds between the proximal end and the distal end, the first sheath having a transition region including a change in flexural modulus of the first sheath along a portion of the length, the transition region being between a first section with a first flexural modulus and a second section with a second flexural modulus, the first flexural modulus being greater than the second flexural modulus and the first section being proximal of the second section, the transition region having a transition region length equal to at least four times a thickness of a wall of the first sheath, wherein the first section and the second section comprise a polymer comprising a polyetheretherketone,
   wherein the distal end of the first sheath is bonded to a second sheath at a bond region, wherein the difference in flexural moduli across the bond region is about 150 ksi or less, wherein the second sheath comprises a material different than the polymer comprising the polyetheretherketone, and wherein the second sheath comprises an ultrasound imaging window, and wherein the second sheath has an outer diameter that is constant along a length of the ultrasound imaging window, and wherein an outer diameter at the bond region is the same as the outer diameter of the second sheath.

18. The catheter of claim 17, wherein the change in the flexural modulus of the first sheath at the transition region between the first section and the second section comprises a continuous gradient along the transition region length.

19. The catheter of claim 17, wherein the crystallinity of the first section is between about 10% and about 40%.

20. The catheter of claim 17, wherein the first section is at least three times the length of the second section.

21. The catheter of claim 17, wherein a thickness of the first sheath is constant along the length.

22. The catheter of claim 17, wherein the second sheath comprises a polyethylene.

23. The catheter of claim 17, wherein the catheter is an ultrasound imaging catheter further including an imaging core in the second sheath.

24. The catheter of claim 23, wherein the imaging core further includes a flexible drive cable, a transducer housing, an ultrasonic transducer stack, and a transmission line.

25. A catheter comprising:
a first sheath having a proximal end and a distal end, and a length extending between the proximal end and the distal end, the first sheath being devoid of any bonds between the proximal end and the distal end, the first sheath having a transition region including a change in a flexural modulus of the first sheath along a portion of the length, the transition region being between a first section with a first flexural modulus and a second section with a second flexural modulus, the first flexural modulus being greater than the second flexural modulus and the first section being proximal of the second section, and the transition region having a transition region length equal to at least two times a thickness of a wall of the first sheath,
wherein the distal end of the first sheath is bonded to a second sheath at a bond region, wherein the difference in flexural moduli across the bond region is about 150 ksi or less, wherein the first sheath comprises a different polymer material than the second sheath, and wherein the second sheath comprises an imaging window.

26. The catheter of claim 25, wherein the first section is longer than the second section such that the transition region is closer to the distal end of the first sheath than to the proximal end of the first sheath.

27. The catheter of claim 25, wherein the first sheath defines a hollow lumen adapted to receive an imaging core therein.

28. The catheter of claim 25, wherein the difference in flexural moduli across the bond region is about 75 ksi or less.

* * * * *